United States Patent
Kaar et al.

(10) Patent No.: US 9,283,338 B2
(45) Date of Patent: Mar. 15, 2016

(54) DOSE COUNTER FOR A METERED-DOSE INHALER

(75) Inventors: Simon G. Kaar, Cork (IE); Jeffrey A. Karg, Hopkinton, MA (US); Timothy Norman Johnson, Raymond, NH (US); Robert Charles Uschold, Leominster, MA (US)

(73) Assignee: IVAX International B.V., Utrecht (NL)

( * ) Notice: Subject to any disclaimer, the term of this patent is extended or adjusted under 35 U.S.C. 154(b) by 313 days.

(21) Appl. No.: 13/387,535

(22) PCT Filed: Jul. 28, 2010

(86) PCT No.: PCT/EP2010/004792
§ 371 (c)(1),
(2), (4) Date: Jun. 8, 2012

(87) PCT Pub. No.: WO2011/012327
PCT Pub. Date: Feb. 3, 2011

(65) Prior Publication Data
US 2012/0240926 A1    Sep. 27, 2012

(51) Int. Cl.
*A61M 11/04* (2006.01)
*A61M 15/00* (2006.01)
(Continued)

(52) U.S. Cl.
CPC ......... *A61M 15/009* (2013.01); *A61M 15/0078* (2014.02); *G06M 1/04* (2013.01); *A61M 15/0073* (2014.02); *A61M 15/0075* (2014.02); *G06M 1/041* (2013.01); *G06M 1/24* (2013.01)

(58) Field of Classification Search
CPC .......... A61M 15/009; A61M 15/0068; A61M 15/0071; A61M 15/0073; A61M 15/0075; A61M 15/0076; A61M 15/0078
USPC ............. 128/200.11, 200.12, 200.13, 200.14, 128/200.15, 200.16, 200.17, 200.18, 128/200.19, 200.21, 200.22, 200.23, 128/200.24, 203.12, 203.15, 205.23
See application file for complete search history.

(56) References Cited

U.S. PATENT DOCUMENTS 6,446,627 B1   9/2002   Bowman
7,819,075 B2   10/2010  Bowman
(Continued)

FOREIGN PATENT DOCUMENTS

CN    1265601 A    9/2000
CN    1946448 A    4/2007
(Continued)

OTHER PUBLICATIONS

European Search Report, dated Jan. 7, 2014, corresponding to counterpart European Patent Application No. 13004775.6.
(Continued)

*Primary Examiner* — Jason Flick
*Assistant Examiner* — Elliot S Ruddie
(74) *Attorney, Agent, or Firm* — RatnerPrestia

(57) ABSTRACT

A dose counter for counting doses of medicament dispensed by or remaining in a metered-dose inhaler. The dose counter includes a rotatably mounted first gear wheel having ratchet teeth and a display coupled to the first gear wheel, the display having a visible array of dose counting indicia indexable in response to rotary motion of the first gear wheel. The dose counter further includes an actuator mechanism having a first ratchet drive pawl for engaging the ratchet teeth of the first gear wheel in response to the dispensation of a medicament dose, and a second ratchet drive pawl for engaging the ratchet teeth of a gear wheel coupled to the display. In use, a first ratchet tooth of the first gear wheel is rotatably driven by the first pawl and then a second ratchet tooth of the gear wheel coupled to the display is rotatably driven by the second pawl.

12 Claims, 11 Drawing Sheets

(51) Int. Cl.
*G06M 1/04* (2006.01)
*G06M 1/24* (2006.01)

(56) References Cited

U.S. PATENT DOCUMENTS

| | | | |
|---|---|---|---|
| 7,832,351 B2 | 11/2010 | Bonney et al. | |
| 2002/0047021 A1 | 4/2002 | Blacker et al. | |
| 2003/0209239 A1* | 11/2003 | Rand et al. | 128/200.23 |
| 2006/0060192 A1* | 3/2006 | Lu | A61M 15/009 128/200.23 |
| 2007/0241025 A1 | 10/2007 | Parkes | |
| 2008/0035144 A1 | 2/2008 | Bowman et al. | |
| 2008/0156321 A1 | 7/2008 | Bowman et al. | |
| 2010/0078490 A1 | 4/2010 | Fenlon | |
| 2012/0247458 A1 | 10/2012 | Lawrence | |

FOREIGN PATENT DOCUMENTS

| | | | |
|---|---|---|---|
| CN | 101198972 A | 6/2008 | |
| GB | 2320489 A | 6/1998 | |
| GB | 2348928 A | 10/2000 | |
| JP | 2007534378 | 11/2005 | |
| WO | WO92/09324 | 6/1992 | |
| WO | 9828033 | 7/1998 | |
| WO | WO 98/56444 A1 | 12/1998 | |
| WO | WO 01/28887 A1 | 4/2001 | |
| WO | WO2005102430 A1 | 11/2005 | |
| WO | WO2006110080 A1 | 10/2006 | |
| WO | 2008015542 | 2/2008 | |
| WO | WO2008/119552 A1 | 10/2008 | |
| WO | WO 2008119552 A1 * | 10/2008 | A61M 15/00 |
| WO | WO2008121459 A1 | 10/2008 | |

OTHER PUBLICATIONS

International Search Report, dated Nov. 4, 2010, International Appl. No. PCT/EP2010/004790, filed Jul. 28, 2010, IVAX Pharmaceuticals Ireland.
International Search Report, dated Oct. 29, 2010, International Appl. No. PCT/EP2010/004791, filed Jul. 28, 2010, IVAX Pharmaceuticals Ireland.
International Search Report, dated Nov. 9, 2010, International Appl. No. PCT/EP2010/004792, filed Jul. 28, 2010, IVAX Pharmaceuticals Ireland.
English translation of Chinese Office Action, dated Apr. 16, 2013, corresponding to counterpart application No. CN 201080041218.1.
English translation of Chinese Office Action, dated Apr. 15, 2013, corresponding to counterpart application No. CN 201080040988.4.
Entire patent prosecution history of U.S. Appl. No. 13/387,508, filed Jun. 8, 2012, entitled, "Dose Counter for a Metered-Dose Inhaler," now U.S. Pat. No. 8,662,381, issued Mar. 4, 2014.
Entire patent prosecution history of U.S. Appl. No. 13/387,532, filed Jun. 8, 2012, entitled, "Dose Counter for a Metered-Dose Inhaler."
Entire patent prosecution history of U.S. Appl. No. 14/132,918 14/132,918, filed, Dec. 18, 2013, entitled, "Dose Counter for a Metered-Dose Inhaler."
European Search Report dated Feb. 7, 2014, for European Patent Application No. 13005367.1.

* cited by examiner

DOSE COUNTER FOR A METERED-DOSE INHALER

CROSS-REFERENCE TO RELATED APPLICATIONS

This application is a U.S. National Phase Patent Application of PCT Application No. PCT/EP2010/004792, filed Jul. 28, 2010, which is incorporated by reference herein in its entirety.

FIELD OF THE INVENTION

This invention relates to a dose counter suitable for inclusion in a metered-dose inhaler. The invention also relates to a metered-dose inhaler which includes the dose counter and a method of counting doses dispensed from a metered-dose inhaler.

BACKGROUND OF THE INVENTION

Metered-dose inhalers include pressurised metered-dose inhalers (of both manually operable and breath-actuated types) and dry-powder inhalers. Such metered-dose inhalers typically comprise a medicament-containing vessel and an actuator body having a drug delivery outlet. The medicament-containing vessel may be a pressurised canister containing a mixture of active drug and propellant. Such canisters are usually formed from a deep-drawn aluminium cup having a crimped ferrule which carries a metering valve assembly. The metering valve assembly is provided with a protruding valve stem which, in use, is inserted as a tight push fit into a so-called "stem block" in the body.

To actuate the conventional manually operable inhaler, the user applies a compressive force to the closed end of the canister. The internal components of the metering valve assembly are spring loaded so that a compressive force of about 15 to 30 N is required to activate the device. In response to this compressive force, the canister moves axially with respect to the valve stem by an amount varying from about 2 to 4 mm. This degree of axial movement is sufficient to actuate the metering valve and cause a metered quantity of the drug and propellant to be expelled through the valve stem. This is then released into the mouthpiece via a nozzle in the stem block. A user inhaling through the drug delivery outlet of the device at this point will thus receive a dose of the drug.

Metered-dose inhalers as described above administer an accurate dose of medicament whenever required, which is particularly useful for users whose respiratory difficulties manifest themselves suddenly. Such has been the success of these devices that they are now used throughout the world.

A more recent development is the so-called breath-actuated metered-dose inhaler which delivers a dose of drug through a mouthpiece in response to inhalation by the user. This type of arrangement is particularly convenient in circumstances where the co-ordination between user inhalation and manual depression of the aerosol canister is imperfect. For example, children sometimes lack the necessary co-ordination to achieve effective self-administration and, at times of respiratory distress, adult users may also experience poor co-ordination.

One of the drawbacks of self-administration from an inhaler, whether manually operated or breath-actuated, is that users often experience difficulty in determining when the charge in the medicament-containing vessel has nearly run out, since the contents of the medicament reservoir are typically invisible to the user. With aerosol canisters, part of the reason for this difficulty is that a surplus of propellant may remain in the canister even though the drug supply is nearly exhausted. Alternatively, the near-exhausted state may result in a surplus of drug in relation to propellant. Thus, the illusion is created that the inhaler is still capable of providing useful doses of medicament simply because the canister contains liquid. This is potentially hazardous for the user since dosing becomes unreliable and because few users routinely carry a back-up device. Many users have several different inhalers for the treatment of a variety of conditions. Others keep inhalers at a number of different locations such as at school, home, work etc. In these circumstances it is particularly difficult for the user to keep track of the amount of usage extracted from each individual inhaler apparatus.

WO 98/28033 discloses a dose counter suitable for use with the above-described metered-dose inhalers. The dose counter enables users to assess how many doses remain in the obscured canister. Such a counter can provide a warning when the inhaler nears exhaustion so that appropriate measures can be taken to avoid running out of medication. Moreover, since the dose counter has a counting resolution of one dose, it can be used for compliance monitoring, either under hospital supervision or by parents and teachers assessing compliance by children in their care. Furthermore, there are regulatory requirements for metered-dose inhalers to have a dose counter in a number of countries.

FIGS. 1 to 3 reproduced herein from WO 98/28033 show the lower portion of a metered-dose inhaler. The inhaler comprises a body 2 having a drug delivery outlet 4. An aerosol canister 6 extends into the lower portion of the body 2. The aerosol canister 6 is formed from a deep-drawn aluminium cup 8 to which a ferrule 10 is attached by crimping.

The lid 10 carries a metering-valve assembly having a protruding valve stem 12, the end of which is received as a tight push fit in a stem block 14 of the body 2. Stem block 14 has a nozzle 16 communicating with the drug delivery outlet 4 so that, upon actuation of the metering-valve assembly, a charge of the drug is emitted through the nozzle 16 into the drug delivery outlet 4. Actuation of the metering-valve assembly is effected by causing downward movement of the aerosol canister 6 relative to the body 2. This may be achieved through manual pressure exerted by the user against the upturned base (not shown) of the aerosol canister 6 or by automatic depression of the aerosol canister 6 in response to user inhalation in inhalers of the breath-actuated type. The mechanism of actuation does not form part of WO 98/28033 or the present invention and will not be described in further detail. A user inhaling through the drug delivery outlet 4 when the aerosol canister 6 is depressed will receive a metered dose of the drug.

With reference to the Figures, a counter mechanism 18 includes an actuator shaft 20 moulded from a plastics material, such as nylon, the actuator shaft 20 having a boss 22 integrally formed at its base. The underside of boss 22 is formed with a blind hole which receives a compression spring 24 mounted on an upstanding spigot 26 formed on a lower element of the counter chassis.

A driver 28 for driving a rotary gear in the form of a ratchet-toothed wheel 30 is integrally moulded with boss 22 of the actuator shaft 20 and comprises a transverse hook element mounted between two arms (only one of which is visible in FIG. 2), the bases of which are conjoined to the boss 22. The transverse hook is dimensioned and oriented to engage with ratchet teeth 32 formed around the periphery of the ratchet-toothed wheel 30 to rotate it in a forward direction.

The ratchet-toothed wheel 30 is integrally moulded with a first hollow axle 34 which is rotatably supported on a first spindle 36 that projects transversely from a chassis sub-element 38. Chassis sub-element 38 also has a second spindle 40 projecting transversely therefrom on which a second hollow axle 42 is rotatably supported. A flexible tape 44 is wound around the second hollow axle 42 which serves as a supply spool and passes to the first hollow axle 34 which serves as a take-up spool (stock bobbin). A guide plate 46 forming part of the chassis sub-element 38 helps to guide the tape 44 in a smooth passage from the supply spool to the take-up spool. The surface of the tape 44 is marked with a progression of descending numbers which denote the number of doses remaining in the aerosol canister. Typically, the starting count is 200 and successive markings on the tape decrease by one. The markings on the tape may decrease by two for every two metered dispenses to allow for larger numbers for easier visibility. The spacing between successive markings is coincident with the indexing motion of the ratchet-toothed wheel 30 so that a new number appears in a window 48 provided in the body 2 for each successive or for every two actuation (s).

The ratchet-toothed wheel 30 and integrally formed first hollow axle 34 are restrained from reverse rotation by a wrap-spring clutch 50 surrounding the hollow axle 34 at the end thereof remote from ratchet-toothed wheel 30. One end (not shown) of the wrap-spring clutch 50 is braced against the counter chassis. The windings of the wrap-spring clutch 50 are oriented such that rotation of the first hollow axle 34 in a forward sense is not resisted by the spring coils. However, reverse rotation of the hollow axle 34 acts so as to tighten the spring coils around it, thereby causing the first hollow axle 34 to be gripped by the internal surface of the wrap-spring clutch 50 and hence restraint from reverse rotation.

FIG. 3 shows a more detailed view of the principal elements of the dose counter 18. It will be seen that the driver 28 comprises the transverse hook 52 mounted between a pair of arms 54, 56 which are joined at their bases by a web. The web is connected to the boss 22 of the actuator shaft 20. A combined actuator and driver assembly may be integrally formed, such as from a plastics material, e.g. as nylon.

In use of the dose counter 18, depression of the canister 6 causes the ferrule 10 to engage with the actuator shaft 20, which actuator shaft 20 moves downwards against the compression spring 24. The transverse hook 52, in turn, engages with the ratchet teeth 32 of the ratchet-toothed wheel 30 which is mounted on the hollow axle 34 serving as the take-up spool for the flexible tape display 44. At the end of the hollow axle 34 remote from the ratchet-toothed wheel 30 is the clutch 50 which serves to restrain the axle 34 against reverse rotation and hence prevents reverse travel of the counter tape 44.

A control surface 58 is depicted in FIG. 3 as a see-through element so that the workings of the dose counter may be more clearly seen. The control surface 58 extends parallel to the direction of travel of the actuator shaft 20 and is located adjacent the ratchet-toothed wheel 30 at a position which marks a chordal projection across one of the wheel faces. One of the support arms 56 of the driver 28 is in sliding contact with control surface 58. This sliding contact serves to inhibit the natural tendency of the driver 28 to flex radially inwardly towards the axis of rotation of the ratchet-toothed wheel 30. By preventing such radially inward flexure, the control surface 58 restricts the engagement and disengagement of the drive 28 with the ratchet-toothed wheel 30 so that the distance by which the ratchet-toothed wheel 30 rotates is limited to one tooth pitch. This condition is observed regardless of the extent of linear travel, or stroke, of the actuator shaft 20.

FIG. 4 shows a schematic view of an alternative arrangement for the ratchet-toothed wheel and driver used in the dose counter 18 described in WO 98/28033. The alternative arrangement uses a reciprocating driver 28 acting in a pushing sense to rotate a ratchet-toothed wheel 30 in the direction shown by the arrows 31. A fixed pawl 60 acts to prevent reverse rotation of the ratchet-toothed wheel 30 by engagement against the trailing edge 62 of a ratchet tooth 32. However, on forward rotation of the ratchet-toothed wheel 30 in the sense of arrows 31, the fixed pawl 60 is capable of radially outward deformation, urged by the leading edge 63 of a ratchet-tooth 32.

In this arrangement, if the ratchet-toothed wheel 30 is rotated by more than a single tooth pitch but by less than two tooth pitches for each reciprocating movement of the driver 28, there is a degree of reverse rotation until the pawl 60 becomes engaged by the trailing edge 62 (as opposed to the leading edge 63) of a ratchet tooth 32. Thus, the rotation of the ratchet-toothed wheel 30 may be described as "stepped".

The components of metered-dose inhalers are manufactured to a high technical specification. However, inevitable variations in the tolerances of the components can, in some circumstances, lead to failure of the dose counter of the type disclosed in WO 98/28033. In a known failure mode, the reciprocating stroke of the canister is insufficient to fully increment the dose counter. This may lead to undercounting, particularly where rotation of the ratchet-toothed wheel is stepped, as illustrated in FIG. 4.

Another problem relates particularly to manually operated metered-dose inhalers. In these types of inhaler, the user cannot be relied upon to repeatably actuate the inhaler with a full reciprocating stroke of the canister. Instead, the user may on some occasions release the canister immediately after the "fire point" of the metering valve, that is to say the point in the stroke at which the medicament is dispensed. This reduced stroke of the canister available for incrementing the dose counter may exacerbate the problem described above.

There is a requirement in the art, therefore, for a dose counter with a reduced failure rate. There is a particular requirement for such a dose counter which can be manufactured efficiently and incorporated into known metered-dose inhalers.

SUMMARY OF THE INVENTION

According to a first aspect of the present invention, there is provided a dose counter for counting doses of medicament dispensed by or remaining in a metered-dose inhaler, the dose counter comprising:
   a rotatably mounted first gear wheel having a circular arrangement of ratchet teeth;
   a display coupled to the first gear wheel, the display having a visible array of dose counting indicia indexable in response to rotary motion of the first gear wheel; and
   an actuator mechanism having a first ratchet drive pawl for engaging the ratchet teeth of the first gear wheel in response to the dispensation of a medicament dose,
   wherein the actuator mechanism further comprises a second ratchet drive pawl for engaging the ratchet teeth of a gear wheel coupled to the display, and wherein the actuator mechanism is configured such that, in use of the dose counter for counting a dispensed dose, a first ratchet tooth of the first gear wheel is engaged and rotatably driven by the first ratchet drive pawl and then a second ratchet tooth of the gear wheel coupled to the display is engaged and rotatably driven by the second ratchet drive pawl.

The counter of the present invention thus provides an actuator mechanism which is able to drive the display sequentially using a pair of ratchet drive pawls. In this way, compared to conventional dose counters having a single ratchet drive pawl, the travel of the gear wheel in response to the dispensation of a medicament can be increased. Alternatively, the travel of the gear wheel can remain unchanged, but the required movement of the first ratchet drive pawl may be decreased.

The reduced requirement for movement of the first ratchet drive pawl may be sufficient for the dose counter to be reliably incremented, even when the medicament canister is released by the user immediately after the fire point, and even when there is a large degree of accumulated variation, or tolerance stack, in the components of the inhaler. Miscounting or non-counting of doses can thereby be avoided, which in turn significantly reduces the failure rate of the dose counter. Dose counters of the type disclosed in WO 98/28033 have been found to be particularly suitable for modification according to the principles of the present invention.

In operating the dose counter, a small increase in actuating force may be required compared to dose counters of the type disclosed in WO 98/28033. For a metered-dose inhaler comprising a pressurised medicament canister, this increase in actuating force generally remains insignificant compared to the force required to overcome the internal valve spring of the canister.

In embodiments of the invention the gear wheel arranged for engagement by the second ratchet drive pawl may either be the first gear wheel or a different gear wheel. In the most preferred embodiments the gear wheel arranged for engagement by the second ratchet drive pawl is the first gear wheel, so that only one gear wheel is required. Where the gear wheel arranged for engagement by the second ratchet drive pawl is a different gear wheel the gear wheels may be mounted at opposite sides of the display.

In a first group of embodiments the gear wheel arranged for engagement by the second ratchet drive pawl is the first gear wheel, and the first and second ratchet drive pawls are defined by a unitary driving member. The driving member is pivotally mounted such that only one of the first and second ratchet drive pawls can be brought into engagement with a ratchet tooth of the first gear wheel at any one time. In this way, the driving member is able to follow a rocking motion according to which the ratchet drive pawls sequentially drive the first gear wheel. The driving member may, for example, have an "escapement" shape whereby the ratchet drive pawls may substantially face each other.

In these embodiments, the actuator mechanism may further comprise an actuator shaft mounted for linear reciprocating movement in response to the dispensing of a dose of medicament. The driving member is then coupled to the actuator shaft such that forwards and reverse strokes of the actuator shaft cause the driving member to rotate in first and (different) second directions, respectively.

In a second group of embodiments, the gear wheel arranged for engagement by the second ratchet drive pawl may either be the first gear wheel or a different gear wheel. The actuator mechanism further comprises an actuator shaft mounted for linear reciprocating movement in response to the dispensing of a dose of medicament. The actuator shaft carries the first ratchet drive pawl, for example in a similar arrangement to that described above with reference to FIG. 3. The first ratchet drive pawl may be arranged between a pair of spaced apart support arms. The second ratchet drive pawl is a separate member, mounted independently of the first ratchet drive pawl. A control surface may be provided to accurately control the points of engagement and disengagement between the first ratchet drive pawl and the first gear wheel.

In these embodiments, the second ratchet drive pawl may be resiliently biased into contact with the ratchet teeth of the gear wheel with which it is arranged for engagement, such that the pawl can be displaced away from the gear wheel against the bias. In particular, the second ratchet drive pawl may be carried by a flexible arm. The second ratchet drive pawl may be configured such that the biasing force is sufficient for the second ratchet drive pawl to drive the gear wheel with which it is arranged for engagement.

The actuator mechanism may, in particular, be configured such that, in use of the dose counter for counting a dispensed dose: a first ratchet tooth of the first gear wheel is engaged and rotatably driven by the first ratchet drive pawl until the second ratchet drive pawl has traveled over the tip of a second ratchet tooth of the gear wheel with which it is arranged for engagement (during which the second ratchet drive pawl may be displaced against its bias); and then the second ratchet tooth of the gear wheel is engaged and rotatably driven by the second ratchet drive pawl (during or after which the first ratchet drive pawl may return to a starting position).

Where the gear wheel arranged for engagement by the second ratchet drive pawl is the first gear wheel, the second ratchet drive pawl may need to be biased in a direction which does not pass through the rotational axis of the gear wheel. Where the gear wheel arranged for engagement by the second ratchet drive pawl is a different (second) gear wheel, the second ratchet drive pawl may be biased in a direction which does pass through the rotational axis of the gear wheel. It will be appreciated, however, that the direction of the biasing force largely depends on the particular geometry of the ratchet teeth of the second gear wheel and the second ratchet drive pawl.

In embodiments of either of the above groups, the actuator shaft may be resiliently biased towards a starting position. The actuator shaft is then displaceable against the resilient bias for actuating the dose counter. The bias may be provided by a compression spring arranged to bear against an underside of the actuator shaft. The actuator shaft may be arranged for both a downwards stroke and an upwards stroke in response to each dispensing of a dose of medicament, i.e. reciprocating movement. In that case, the dose counter may be actuated on either the downwards or the upwards stroke of the actuator shaft.

The second ratchet drive pawl may be arranged such that it prevents reverse rotation of the gear wheel(s). Alternatively, the dose counter may be provided with a separate means to prevent reverse rotation of the gear wheel, such as another pawl arranged to engage the ratchet teeth of the gear wheel.

The display may comprise a flexible tape arranged between an indexing spool and a stock bobbin. The dose counting indicia of the display may include a unique indicium for display after each and every dose has been dispensed. The dose counting indicia may comprise at least 50 unique dose counting indicia representative of a number of doses dispensed by or remaining in the inhaler.

According to a second aspect of the present invention, there is provided a metered-dose inhaler, such as a manually-operated metered-dose inhaler, comprising:
  a medicament canister;
  an actuator body for receiving the canister and having a medicament delivery outlet; and
  the dose counter described above.

According to a third aspect of the invention, there is provided a method of counting doses dispensed from or remaining in a metered-dose inhaler, the dose counter comprising:
  a rotatably mounted first gear wheel having a circular arrangement of ratchet teeth;

a display coupled to the first gear wheel, the display having a visible array of dose counting indicia indexable in response to rotary motion of the first gear wheel; and an actuator mechanism having a first ratchet drive pawl for engaging the ratchet teeth of the first gear wheel in response to the dispensation of a medicament dose, and a second ratchet drive pawl for engaging the ratchet teeth of a gear wheel coupled to the display, the method comprising:

engaging and rotatably driving a first ratchet tooth of the first gear wheel with the first ratchet drive pawl; and engaging and rotatably driving a second ratchet tooth of the gear wheel coupled to the display with the second ratchet drive pawl.

The third aspect of the invention corresponds to use of the does counter or metered-dose inhaler described above. As such, the method may include using any of the features of the dose counter described above.

BRIEF DESCRIPTION OF THE DRAWINGS

The present invention will now be described, by way of example only, with reference to the accompanying drawings, in which.

DETAILED DESCRIPTION

Figure 1:
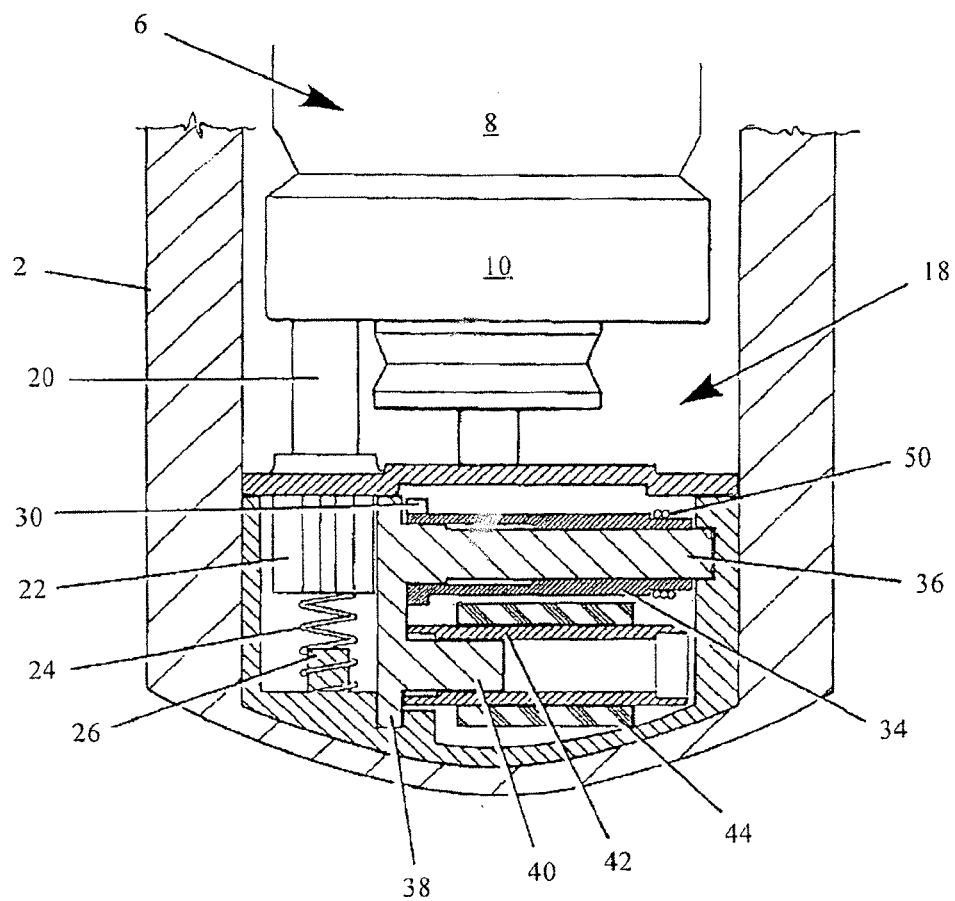
FIGS. 1, 2, 3 and 4 are each views of a dose counter for a metered-dose inhaler according to the prior art document WO 98/28033.
Figure 2:
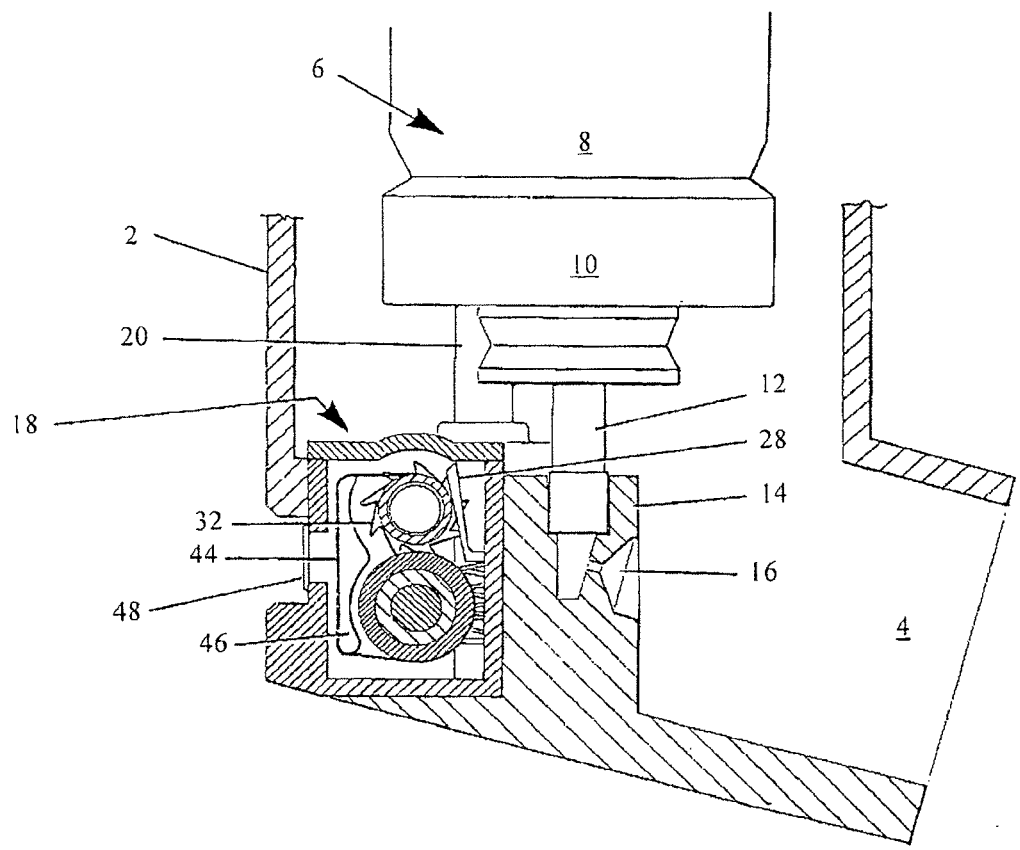
Figure 3:
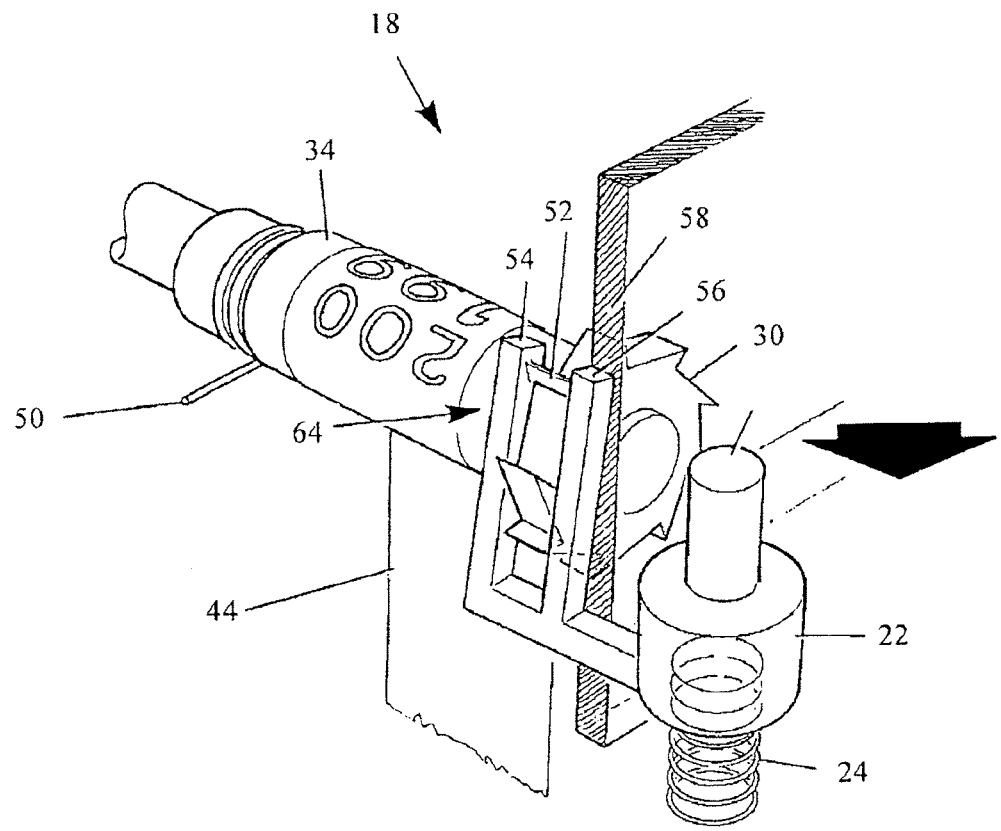
Figure 4:
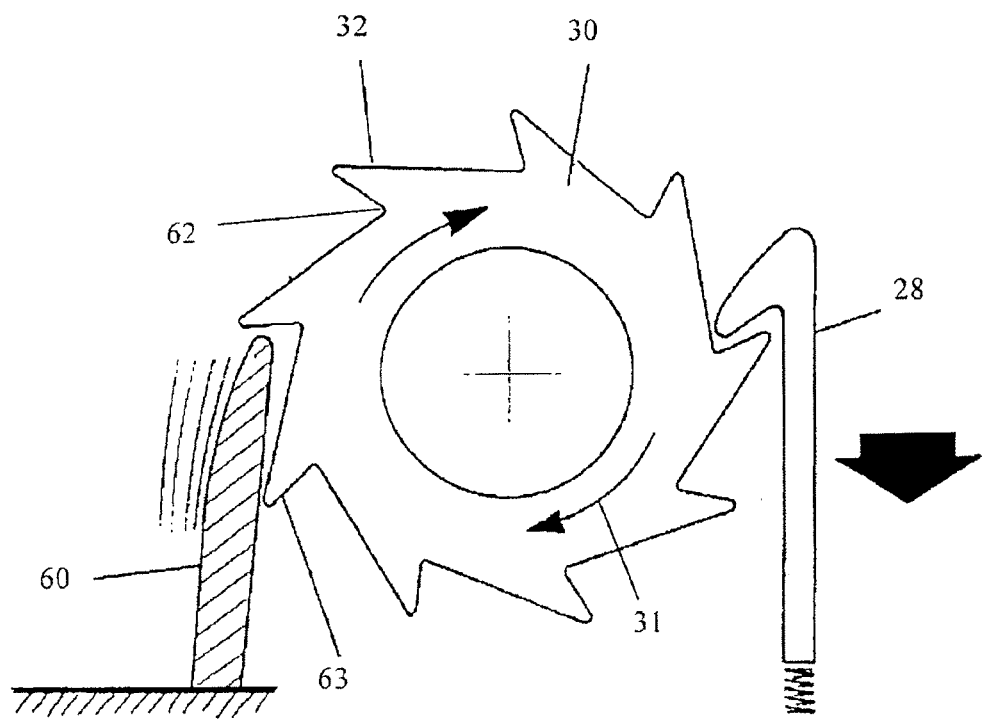

Dose counters of the present invention are based on that shown in FIGS. 1 to 4 described hereinabove, except that the actuator mechanism is modified. Thus, the invention generally provides a dose counter comprising a rotatably mounted gear wheel having a circular arrangement of ratchet teeth and a display coupled to the gear wheel. The display has a visible array of dose counting indicia indexable in response to rotary motion of the gear wheel. The dose counter also comprises an actuator mechanism having a first ratchet drive pawl for engaging the ratchet teeth of the first gear wheel in response to the dispensation of a medicament dose.

According to the invention, the actuator mechanism further comprises a second ratchet drive pawl for engaging the ratchet teeth of a gear wheel coupled to the display. The actuator mechanism is configured such that, in use of the dose counter for counting a dispensed dose, a first ratchet tooth of the first gear wheel is engaged and rotatably driven by the first ratchet drive pawl and then a second ratchet tooth of the gear wheel coupled to the display is engaged and rotatably driven by the second ratchet drive pawl.

A first dose counter according to the present invention will now be described with reference to FIGS. 5 to 7d. The actuator mechanism 118 of the dose counter is shown schematically in FIG. 5, together with the first gear wheel in the form of a ratchet-toothed wheel 30. The dose counter display is essentially the same as that illustrated in FIGS. 1 to 3 and includes a flexible tape 44 arranged between an indexing spool 34 and a stock bobbin 42.

The ratchet-toothed wheel 30 has the same configuration as that of the corresponding wheel 30 illustrated in FIGS. 1 to 4. Thus, a plurality of ratchet teeth 32 are arranged about a circular periphery of the wheel 30. The ratchet-toothed wheel 30 is integrally moulded with a hollow axle 34 serving as the indexing spool of the display. The hollow axle 34 is rotatably supported on a spindle that projects from the chassis of the dose counter.

Figure 5:
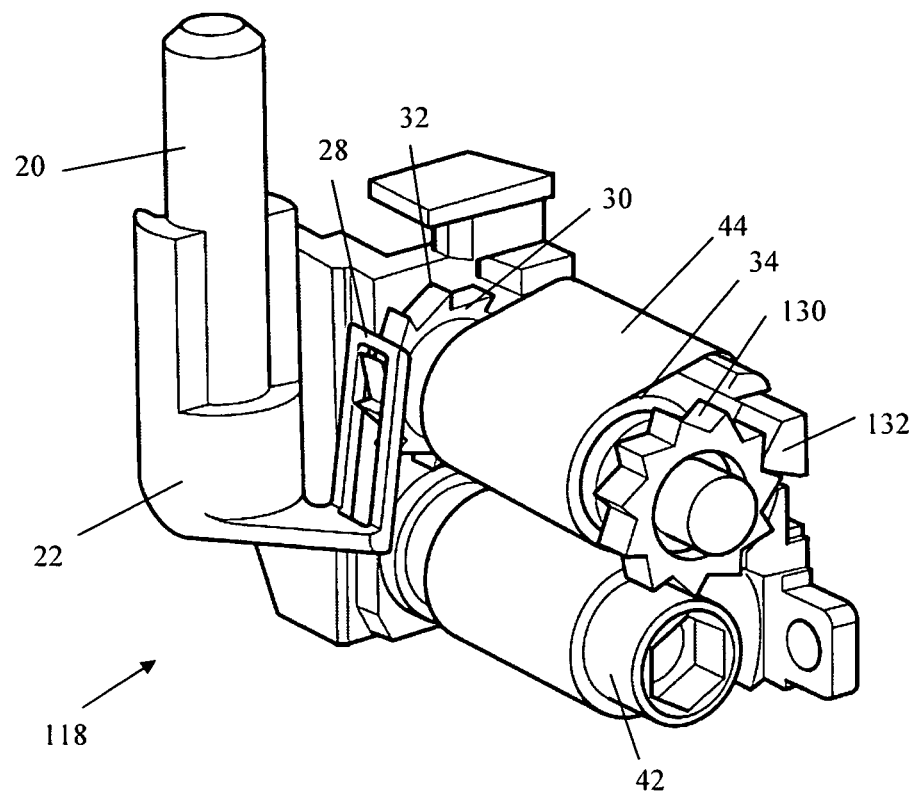
FIG. 5 is a perspective view of a first dose counter according to the present invention.
Figure 6:
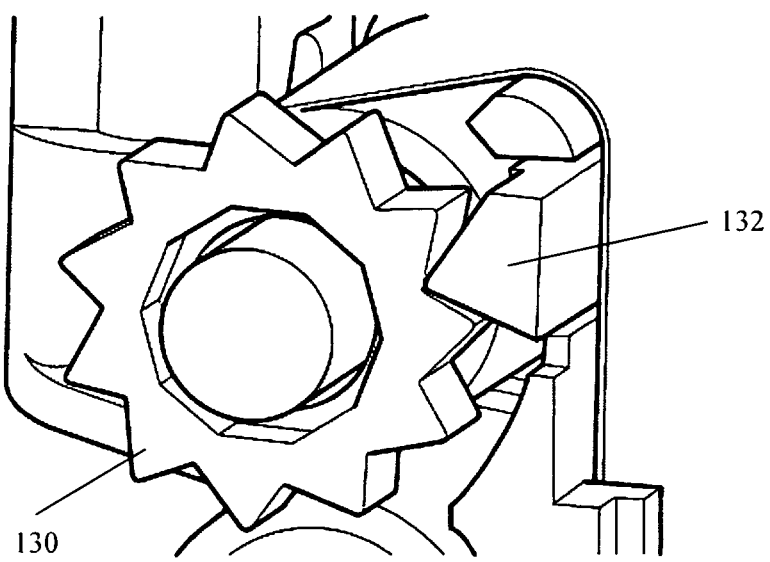
FIG. 6 is a perspective view showing elements of the first dose counter shown in FIG. 5 in greater detail.

The actuator mechanism 118 of the first dose counter according to the invention is similar to the actuator mechanism shown in FIGS. 1 to 4 in many respects. Thus, the mechanism 118 comprises an actuator shaft 20 mounted for reciprocal linear movement in a longitudinal direction. In common with the shaft shown in FIGS. 1 and 2, a top portion (not shown) of the actuator shaft 120 is arranged for engagement by a medicament canister of the metered dose inhaler with which the dose counter is used. The actuator shaft 20 has a boss 22 integrally formed at its base, the underside of which is formed with a blind hole which receives a compression spring. The compression spring serves to bias the actuator shaft 20 into an upwards (starting) position, as shown in FIG. 5.

A driver in the form of a ratchet drive pawl 28 is integrally formed with the boss 22 of the actuator shaft 20 for driving the ratchet-toothed wheel 30. The driver comprises a first ratchet drive pawl 28 extending in a transverse direction and supported by a pair of arms. The first ratchet drive pawl 28 is dimensioned and orientated for suitable engagement with the ratchet teeth 132 of the ratchet-toothed wheel 130.

The actuator mechanism 118 of the first dose counter differs from the actuator mechanism shown in FIGS. 1 to 4 in that there is no fixed pawl for preventing reverse rotation of the ratchet-toothed wheel 30. Instead the mechanism 118 is provided with a second ratchet drive pawl 132 arranged for engagement with a second gear wheel 130, as shown more clearly in FIG. 6.

In common with the ratchet-toothed wheel 30, the second gear wheel 130 is integrally moulded with the hollow axle 34 that serves as the indexing spool of the display. The ratchet-toothed wheel 30 and the second gear wheel 130 are arranged at opposite ends of the hollow axle 34 on either side of the flexible display tape 44 so that either wheel 130, 30 can be used to drive the display. In this embodiment, the second gear wheel 130 has triangular-shaped teeth. It can be appreciated that the teeth on gear wheel 130 may have varying shapes that promote rotation similarly.

The second ratchet drive pawl 132 not only prevents reverse rotation of the second gear wheel 130 and (indirectly) the ratchet-toothed wheel 30, but is also configured to drive the second gear wheel 130 (and thus the display) in response to the dispensation of a medicament dose. The second ratchet drive pawl 132 is therefore dimensioned and orientated for suitable engagement with the teeth of the second gear wheel 130, an engagement portion of the second ratchet drive pawl 132 being wedge-shaped.

The second ratchet drive pawl 132 is provided with a resilient mounting so that it is biased into contact with the teeth of the second gear wheel 130. The resilient mounting comprises a flexible arm (not shown), a proximal end of which is mounted to the dose counter chassis and a distal end of which carries the second ratchet drive pawl 132. The resilient mounting is configured such that the biasing force is in a direction substantially towards the rotational axis of the second gear wheel 130. The second ratchet drive pawl 132 can be displaced away from the second gear wheel 130 against the resilient bias.

It will be appreciated that the mounting of the second ratchet drive pawl 132 is completely independent from the mounting of the first ratchet drive pawl 28 described above.

Use of the first dose counter according to the invention for counting doses dispensed from a metered-dose inhaler will now be described with reference to FIGS. 7a to 7d. FIGS. 7a to 7d are schematic diagrams showing components that are illustrated in FIG. 5 at different stages of the actuation cycle. The left hand side of each diagram illustrates the ratchet-toothed wheel 30 and the first ratchet drive pawl 28. The right hand side of each diagram illustrates the second gear wheel 130 and the second ratchet drive pawl 132.

The metered-dose inhaler is actuated by the user applying a manual compressive force to the closed end of a medicament canister (not shown). In response to this compressive force, the canister moves axially downwards with respect to its valve stem by an amount varying from about 2 to 4 mm. Approximately 2 mm of displacement is required to fire the valve and dispense a dose of medicament. After the medicament has been dispensed, the user releases the compressive force and the canister returns to its starting position under the action of the internal valve spring. The dose counter is driven by the reciprocating linear movement of the canister as the medicament dose is dispensed.

Figure 7A:
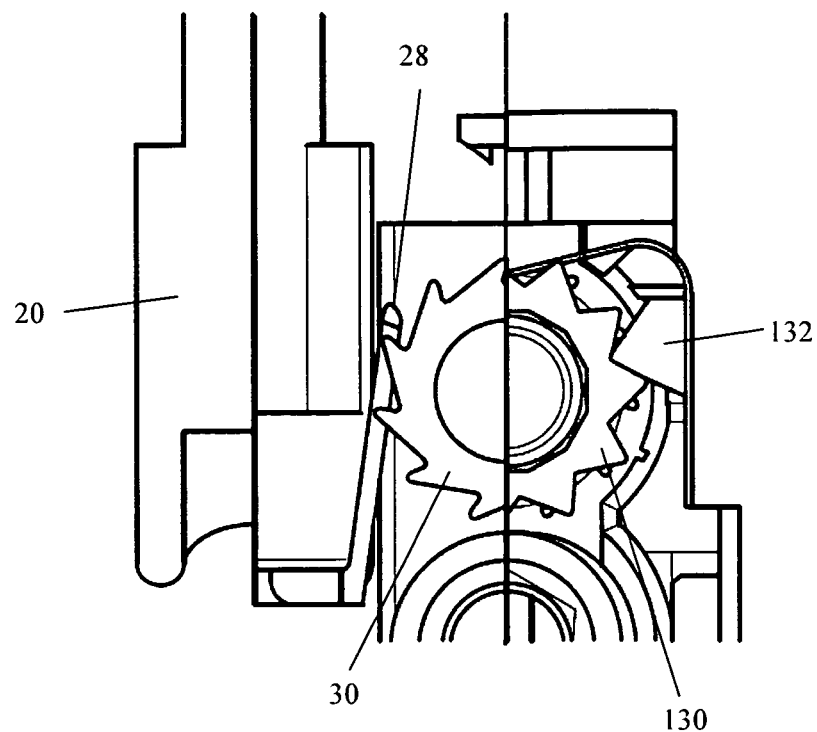
FIGS. 7a, 7b, 7c and 7d are each diagrams for use in explaining the operation of the first dose counter shown in FIG. 5.

FIG. 7a shows the starting position of the dose counter. In this position the actuator shaft 20 is biased upwards into its starting position. The first ratchet drive pawl 28 is positioned a small distance above a tooth of the ratchet-toothed wheel 30 and the second ratchet drive pawl 132 is positioned between two adjacent gear teeth of the second gear wheel 130.

Figure 7B:
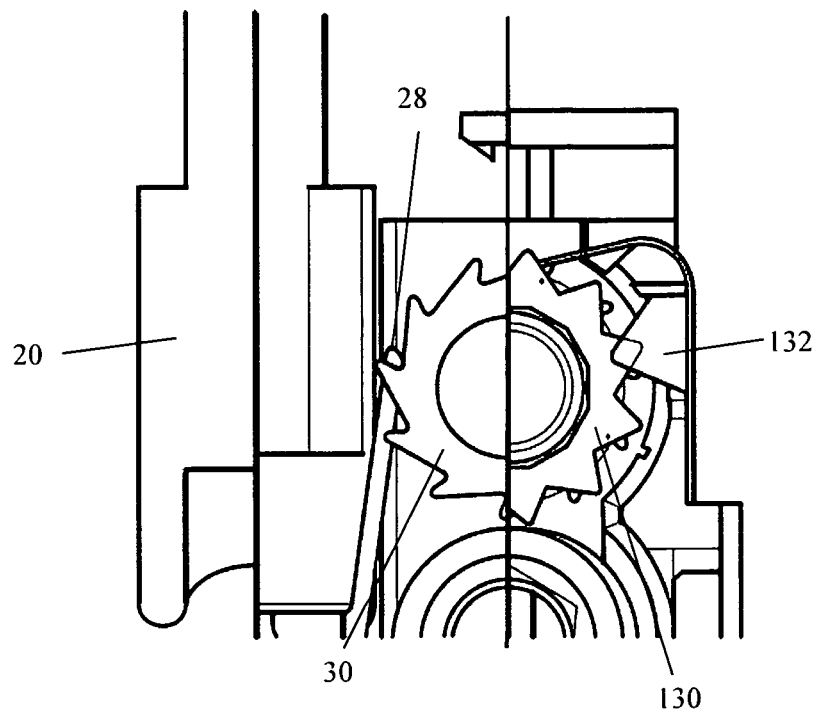

The downwards movement of the medicament canister during the dispensing of a medicament dose causes the ferrule of the canister to engage with and linearly displace the actuator shaft 20 downwards. The displacement of the actuator shaft 20 causes the first ratchet drive pawl 28 to move downwards by a short distance until the pawl 28 engages the tooth of the ratchet-toothed wheel 30. This engagement rotatably drives the ratchet-toothed wheel 30 and the second gear wheel 130 by about half of the angle required for reliable indexing of the dose counter, as shown in FIG. 7b. The rotation of the second gear wheel 130 causes the second ratchet drive pawl 132 to be displaced away from the second gear wheel 130, against the resilient bias, as the leading edge of the pawl 132 slides along a first face of a gear tooth. At the end of the downwards stroke of the actuator shaft 20 the leading edge of the second drive pawl 132 just clears the tip of the tooth of the second gear wheel 130 (the schematic diagram of FIG. 7b shows the second ratchet drive pawl 132 to be fixed, but in practice it would be displaced to the right).

Figure 7C:
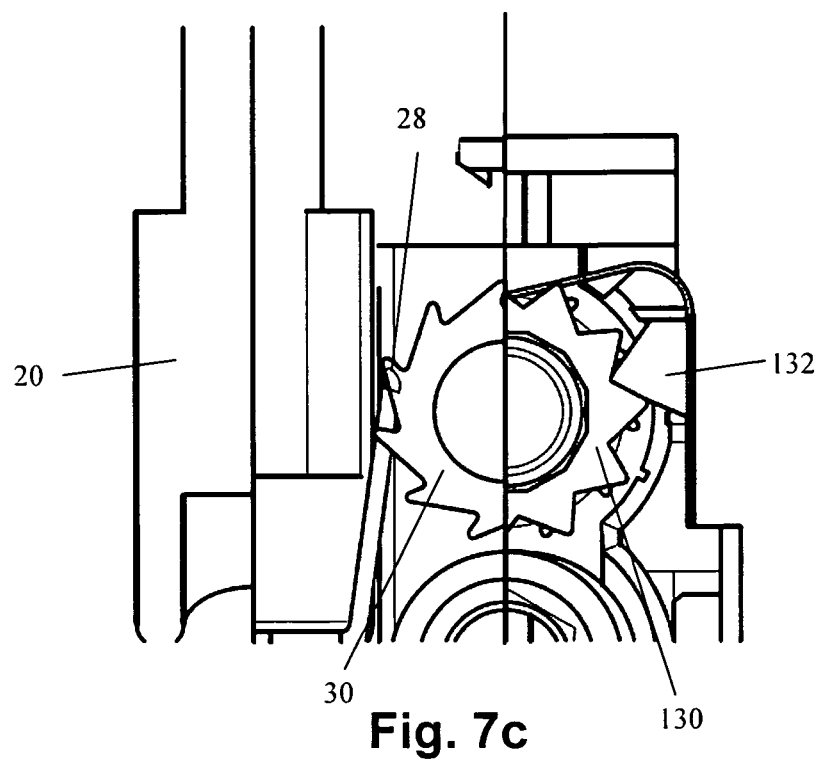

At this stage, the resilient mounting of the second ratchet drive pawl 132 urging the pawl 132 against a second face of the gear tooth of the second gear wheel 130 is sufficient to drive the second gear wheel 130 and (indirectly) the ratchet-toothed wheel 30 by the remainder of the angle required for reliable indexing of the dose counter. Rotation of the second gear wheel 130 ends when the leading edge of the second ratchet drive pawl 132 is positioned between two adjacent gear teeth of the gear wheel 130, as shown in FIG. 7c. In this way, the second ratchet drive pawl 132 can be said to provide "stepped" rotation of the second gear wheel 130 and the ratchet-toothed wheel 30.

Figure 7D:
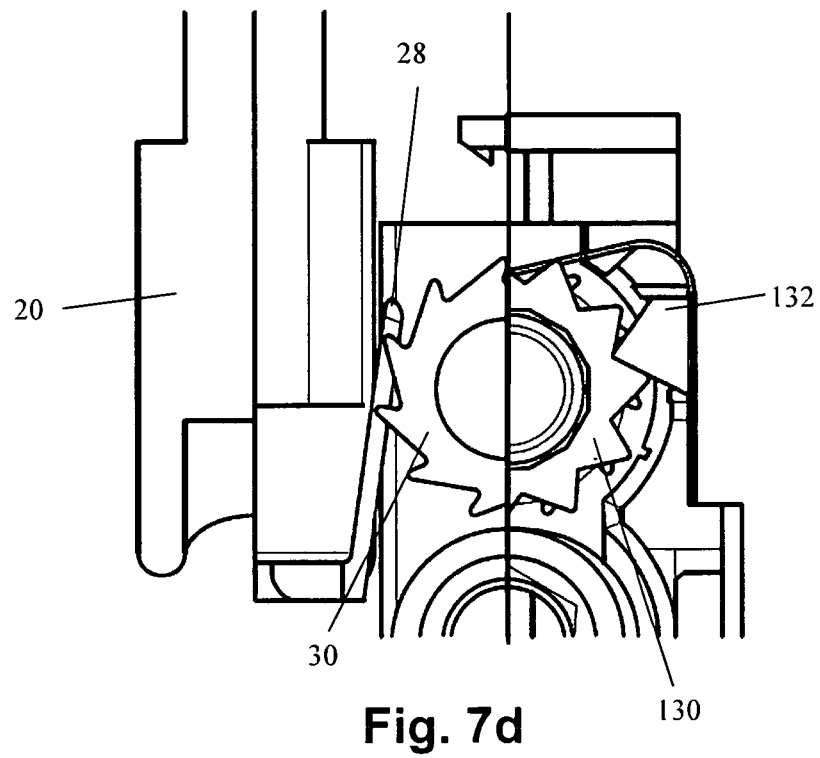

FIG. 7d shows the configuration of the actuator mechanism 118 after the actuator shaft 20 has been allowed to return to its starting position. Essentially, the actuator shaft 20 moves upwards, carrying the first ratchet drive pawl 28, with the first ratchet drive pawl 28 flexing away from the ratchet-toothed wheel 30 as it moves upwards.

By driving the display using the two ratchet drive pawls 28, 132 the required linear displacement of the actuator shaft 20 can be reduced. This reduces the risk of miscounting, particularly undercounting and, in turn, reduces the failure rate of the dose counter. The reduction in the required linear displacement of the actuator shaft 20 is particularly advantageous for manually operated metered-dose inhalers, since the linear input stroke with this type of inhaler may be as small as 1.5 mm when the medicament canister is released immediately after the fire point of the valve has been reached.

The reduction in the required stroke of the actuator shaft can also reduce the risk of miscounting due to accumulated tolerance stacks and lost motion, as will be explained with reference to FIGS. 8a to 8c.

Figures 8A, 8B, 8C:
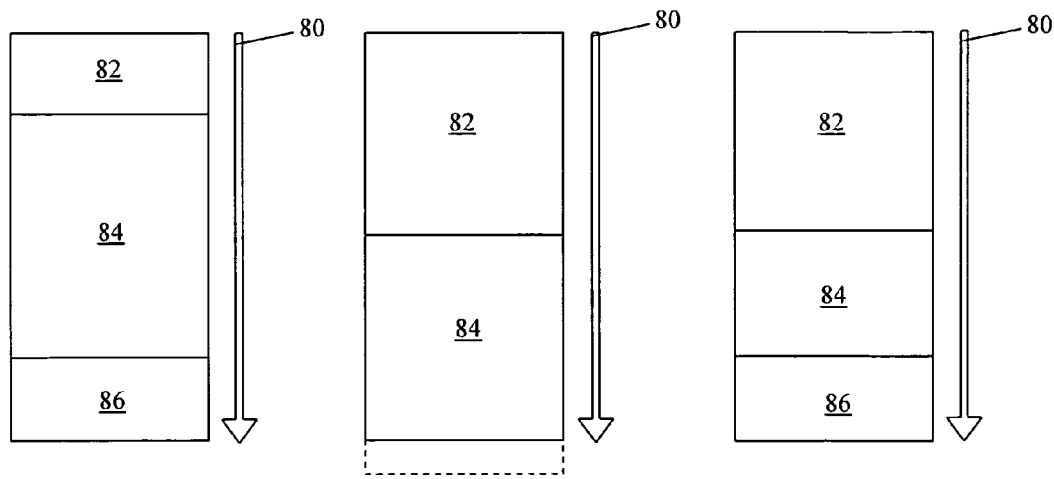
FIGS. 8a, 8b and 8c are each graphical representations of medicament canister travel during actuation of three metered-dose inhalers.

FIG. 8a is a graphical representation of the travel 80 of the medicament canister of a first inhaler having a working dose counter of the type shown in FIGS. 1 to 4. A first portion of the travel 82 takes up the accumulated tolerances of the manufactured components and any lost motion. A second portion of the travel 84 is the travel required to increment the dose counter. A third portion of the travel 86 is "excess" travel which would have been available had the accumulated tolerances or lost motion been greater.

FIG. 8b is a graphical representation of the travel 80 of the medicament canister of a second inhaler having a non-working (failed) dose counter of the type shown in FIGS. 1 to 4. The total canister travel 80 is the same as that for the first inhaler shown in FIG. 8a. Again, a first portion of the travel 82 takes up the accumulated tolerances of the manufactured components and any lost motion. The accumulated tolerances and lost motion are significantly greater in the second inhaler than they were in the first inhaler, so that the first portion of the travel 82 is correspondingly greater. A second portion of the travel 84 is the travel required to increment the dose counter, and this is the same as that shown in FIG. 8a for the first inhaler. However, there is insufficient remaining canister travel 80 to increment the dose counter, which causes the dose counter to fail.

FIG. 8c is a graphical representation of the travel 80 of the medicament canister of a third inhaler having the dose counter according to the invention shown in FIG. 5. The total canister travel 80 is the same as that for the first and second inhalers shown in FIGS. 8a and 8b. Again, a first portion of the travel 82 takes up the accumulated tolerances of the manufactured components and any lost motion. The accumulated tolerances and lost motion are the same as those of the second inhaler which led to failure of the second inhaler's dose counter. A second portion of the travel 84 is the travel required to increment the dose counter. This second portion of the travel 84 is significantly less than it is for the first and second inhalers shown in FIGS. 8a and 8b, since the second portion of the travel 84 is reduced by the action of the second ratchet drive pawl. Consequently, there is sufficient remaining canister travel 80 to increment the dose counter and the dose counter does not fail. A third portion of the travel 86 is the "excess" travel which would have been available had the accumulated tolerances or lost motion been even greater.

Thus, it will be seen that the action of the second ratchet drive pawl of the invention can lead to a reduction in failures caused by excessive accumulated tolerances and lost motion.

The provision of the second ratchet drive pawl according to the principles of the present invention may lead to a small increase in the force with which the medicament canister must be depressed. The force required for operating the dose counter, however, generally remains small compared to the force that is required to overcome the canister's internal valve spring.

Figure 9:
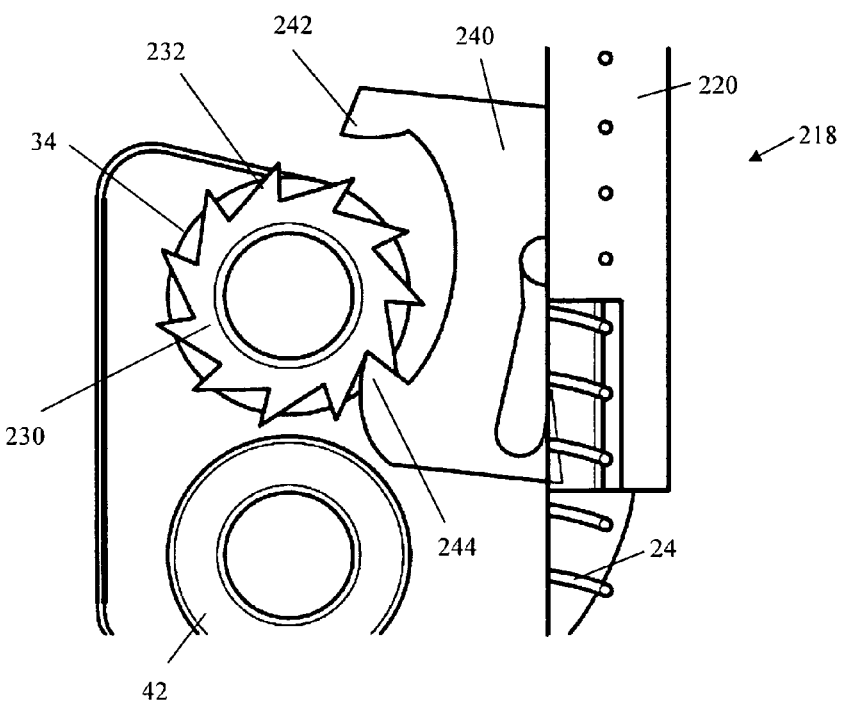
FIG. 9 is a schematic side view of a second dose counter according to the present invention.

A second dose counter according to the present invention will now be described with reference to FIGS. 9 to 10e. The actuator mechanism 218 of the dose counter is shown schematically in FIG. 9, together with the first gear wheel in the form of a ratchet-toothed wheel 230. The dose counter display is essentially the same as that illustrated in FIGS. 1 to 3 and includes a flexible tape (not shown) arranged between an indexing spool 34 and a stock bobbin 42.

The ratchet-toothed wheel 230 has a similar configuration as that of the corresponding wheel 30 illustrated in FIGS. 1 to 4. Thus, a plurality of ratchet teeth 232 are arranged about a circular periphery of the wheel 230. The ratchet-toothed wheel 230 is integrally moulded with a hollow axle 34 serving as the indexing spool of the display. The hollow axle 34 is rotatably supported on a spindle that projects from the chassis of the dose counter. Compared to the ratchet-toothed wheel 30 shown in FIGS. 1 to 4, the teeth 232 of the ratchet toothed wheel 230 are modified, as will be explained in more detail hereinbelow.

The actuator mechanism 218 of the second dose counter is similar to the actuator mechanism shown in FIGS. 1 to 4 in some respects. Thus, the mechanism 218 comprises an actuator shaft 220 mounted for reciprocal linear movement in a longitudinal direction. In common with the actuator shaft shown in FIGS. 1 and 2, a top portion (not shown) of the actuator shaft 220 is arranged for engagement by a medicament canister of the metered dose inhaler with which the dose counter is used. The base of the actuator shaft 220 is formed with a blind hole which receives a compression spring 24. The compression spring 24 serves to bias the actuator shaft 220 into an upwards (starting) position, as shown in FIG. 9.

The actuator mechanism 218 of the second dose counter differs from the actuator mechanism shown in FIGS. 1 to 4 in that there is no fixed pawl for preventing reverse rotation of the ratchet-toothed wheel 230. Instead, the mechanism 218 is provided with a pivotally mounted driving member 240 defining first and second ratchet drive pawls 242, 244. The driving member 240 is coupled to the actuator shaft such that forwards (downwards) and reverse (upwards) strokes of the actuator shaft 220 cause the driving member to rotate in anticlockwise and clockwise directions, respectively (as viewed in FIG. 9). In other words, the reciprocating movement of the actuator shaft 220 causes a rocking movement of the driving member 240. Suitable mechanisms for converting the reciprocating movement into the rocking movement will be well known to those skilled in the art. The pivotal axis of the driving member 240 is parallel to the rotational axis of the ratchet-toothed wheel 230.

The driving member 240 is a plate-like component moulded from a rigid plastics material. The member has an "escapement" configuration whereby only one of the first and second ratchet drive pawls 242, 244 can be brought into engagement with a ratchet tooth of the first gear wheel 230 at any one time. The ratchet drive pawls 242, 244 substantially face each other and are equidistant from the pivotal axis of the driving member 240. The ratchet drive pawls 242, 244 are dimensioned and shaped such that engagement of the teeth of the ratchet-toothed wheel 230 by either pawl 242, 244 may drive the ratchet-toothed wheel in a clockwise direction (as viewed in FIG. 9). Thus, the rocking movement of the driving member 240 may cause the ratchet drive pawls 242, 244 to sequentially drive the ratchet-toothed wheel 230 and, therefore, the dose counter display. The ratchet drive pawls 242, 244 also serve to prevent reverse rotation of the ratchet-toothed wheel 230.

Use of the second dose counter according to the invention for counting doses dispensed from a metered-dose inhaler will now be described with reference to FIGS. 10a to 10e. FIGS. 10a to 10e are schematic diagrams showing components that are illustrated in FIG. 9 at different stages of the actuation cycle.

The metered-dose inhaler is actuated by the user applying a manual compressive force to the closed end of a medicament canister (not shown). In response to this compressive force, the canister moves axially downwards with respect to its valve stem by an amount varying from about 2 to 4 mm. Approximately 2 mm of displacement is required to fire the valve and dispense a dose of medicament. After the medicament has been dispensed, the user releases the compressive force and the canister returns to its starting position under the action of the internal valve spring. The dose counter is driven by the reciprocating linear movement of the canister as the medicament dose is dispensed.

Figure 10A:
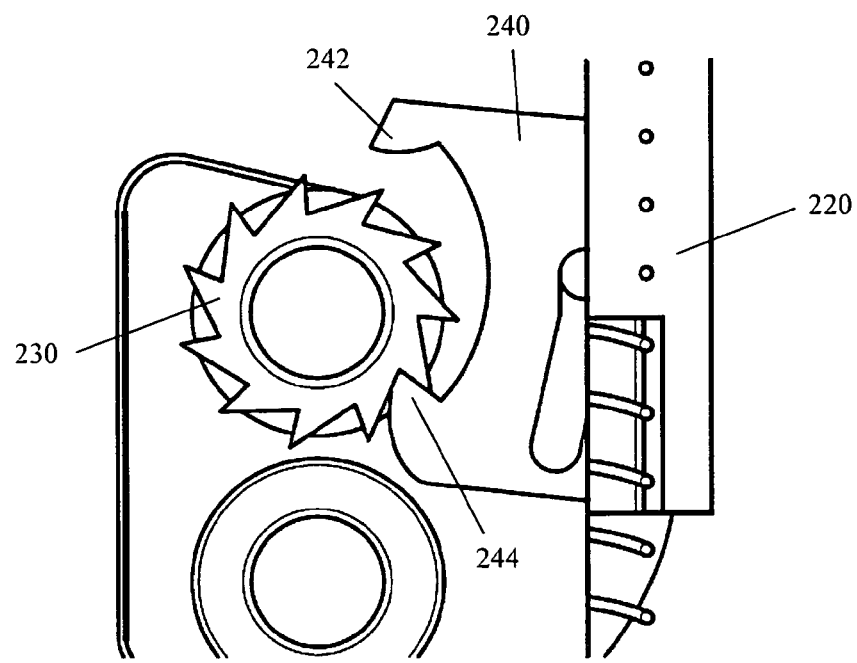
FIGS. 10a, 10b, 10c, 10d and 10e are each diagrams for use in explaining the operation of the second dose counter shown in FIG. 9.

FIG. 10a shows the starting position of the dose counter. In this position the actuator shaft 230 is biased upwards into its starting position. The driving member 240 is rotated to the maximum clockwise extent so that the first ratchet drive pawl 242 is positioned away from the teeth of the ratchet-toothed wheel 230 and the second ratchet drive pawl 244 is positioned between two adjacent teeth of the ratchet-toothed wheel 230.

Figure 10B:
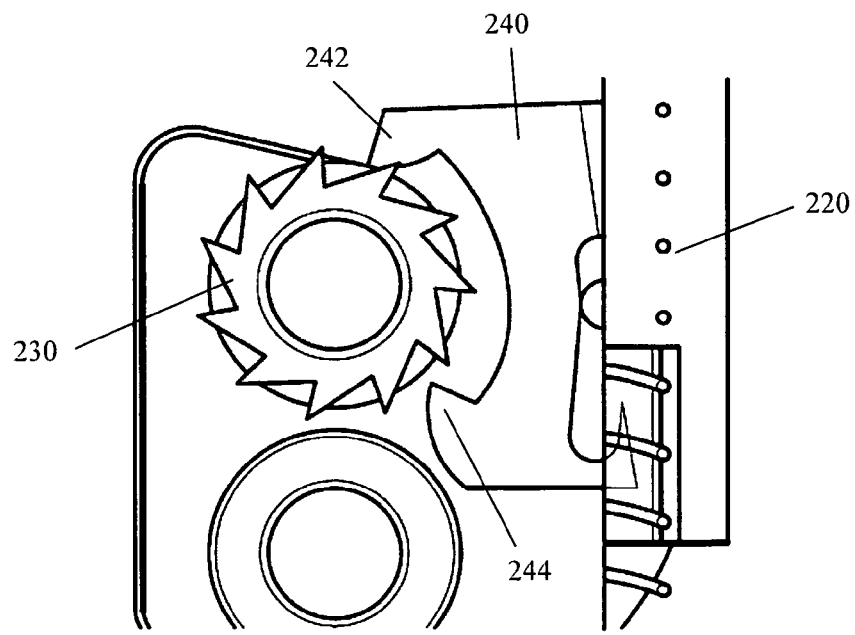
Figure 10C:
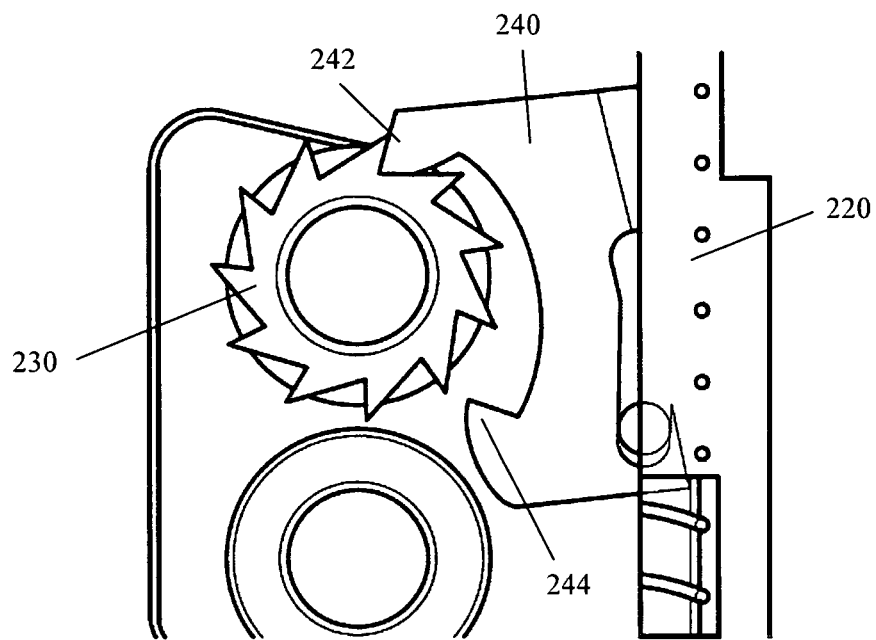

The downwards movement of the medicament canister during the dispensing of a medicament dose causes the ferrule of the canister to engage with and linearly displace the actuator shaft 220 downwards. The downwards displacement of the actuator shaft 220 causes the driving member 240 to move in an anticlockwise direction, as shown in FIG. 10b. As such, the first ratchet drive pawl 242 moves into engagement with a tooth of the ratchet-toothed wheel 230 and the second ratchet drive pawl 244 moves away from the teeth of the ratchet-toothed wheel 230. The engagement by the first ratchet drive pawl 242 drives the ratchet-toothed wheel 230 in a clockwise direction by about half of the angle required for reliable indexing of the dose counter, as shown in FIG. 10c. FIG. 10c shows the driving member 240 rotated to the maximum anticlockwise extent and corresponds to the position when the actuator shaft 220 reaches the bottom of its travel.

Figure 10D:
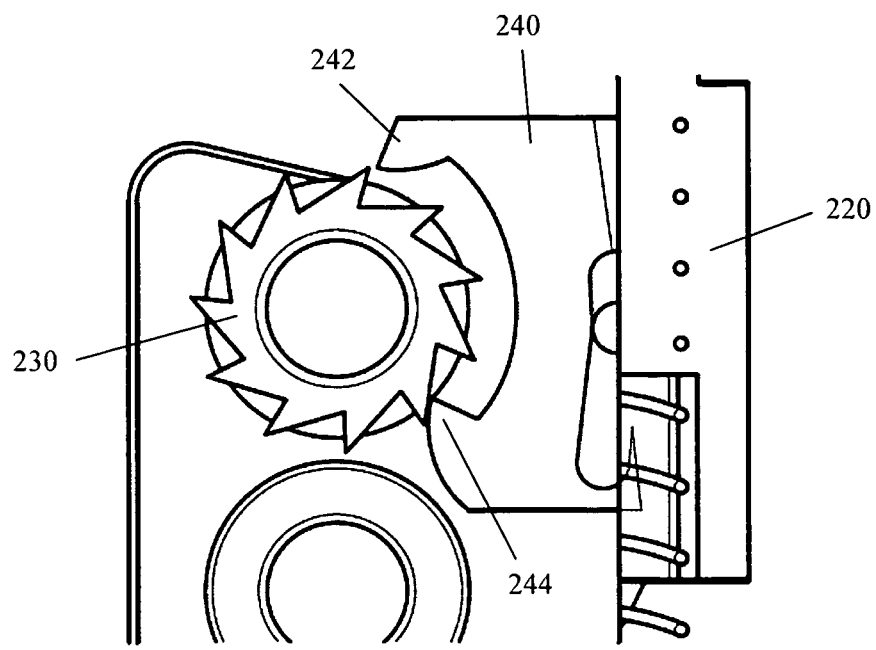

After dispensation of a medicament dose the user releases the compressive force on the medicament canister and the canister returns to its starting position under the action of the internal valve spring, allowing the actuator shaft 220 to move upwards. The upwards displacement of the actuator shaft 220 causes the driving member 240 to move in a clockwise direction, as shown in FIG. 10d. As such, the second ratchet drive pawl 244 moves into engagement with a tooth of the ratchet-toothed wheel 230 and the first ratchet drive pawl 242 moves away from the teeth of the ratchet-toothed wheel 230. The engagement by the second ratchet drive pawl 244 further drives the ratchet-toothed wheel 230 in a clockwise direction by the remainder of the angle required for reliable indexing of the dose counter. It will be appreciated that the first and second ratchet drive pawls 242, 244 are arranged to engage and drive opposite same faces of the teeth of the ratchet-toothed wheel 230.

Figure 10E:
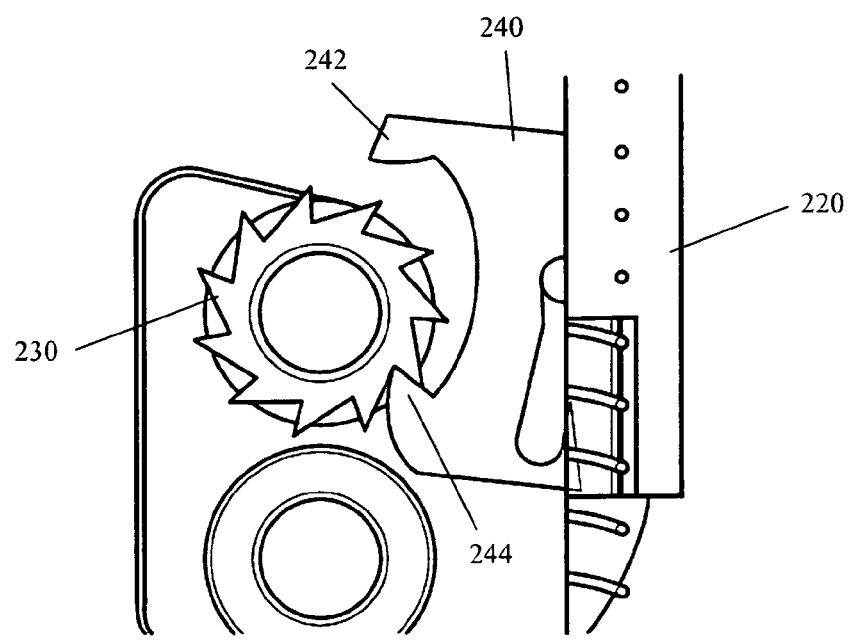

FIG. 10e shows the dose counter after it has returned to its starting position. Thus, the actuator shaft 220 is biased upwards into its starting position. The driving member 240 is rotated to the maximum clockwise extent so that the first ratchet drive pawl 242 is positioned away from the teeth of the ratchet-toothed wheel 230 and the second ratchet drive pawl 244 is positioned between two adjacent teeth of the ratchet-toothed wheel 230. In this way, the driving member 240 can be said to provide "stepped" rotation of the ratchet-toothed wheel 230.

By driving the display using the two ratchet drive pawls 242, 244 the required linear displacement of the actuator shaft 220 can be reduced. This reduces the risk of miscounting, particularly undercounting and, in turn, reduces the failure rate of the dose counter. The reduction in the required linear displacement of the actuator shaft 220 is particularly advantageous for manually operated metered-dose inhalers, since the linear input stroke with this type of inhaler may be as small as 1.5 mm when the medicament canister is released immediately after the fire point of the valve has been reached. The reduction in the required stroke of the actuator shaft can also reduce the risk of miscounting due to accumulated tolerance stacks and lost motion.

Figure 11:
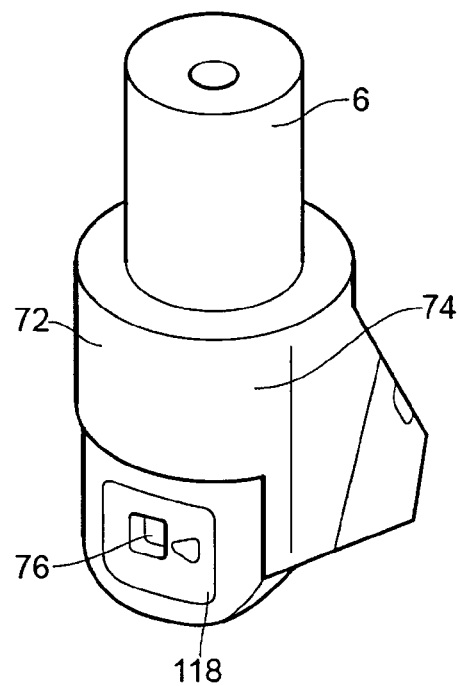
FIG. 11 is a view of a metered-dose inhaler according to the invention.

The present invention further provides a metered-dose inhaler 72 as shown in FIG. 11. The inhaler comprises a medicament canister 6, an actuator body 74 for receiving the canister 6 and having a medicament delivery outlet, and the dose counter as described hereinabove. The actuator body 74 has a window 76 for viewing the display. In a preferred embodiment the actuator body 74 comprises a sump, and preferably a smooth rounded sump. The rounded sump may have a substantially cylindrical upper portion and a substantially hemi-spherical lower portion. By providing a smooth sump the internal surfaces are sufficiently free of protrusions so that during normal use medicament will not substantially adhere thereto.

The medicament canister 6 may contain a medicament in the form of an aerosol. The medicament may be any medicament that is suitable to be delivered to a patient via a metered-dose inhaler. In particular medicaments for the treatment of a wide variety of respiratory disorders are delivered in this manner including anti-allergic agents (e.g. cromoglycate, ketotifen and nedocromil), anti-inflammatory steroids (e.g. beclomethasone dipropionate, fluticasone, budesonide, flunisolide, ciclesonide, triamcinolone acetonide and mometasone furoate); bronchodilators such as: [beta]2-agonists (e.g. fenoterol, formoterol, pirbuterol, reproterol, salbutamol, salmeterol and terbutaline), non-selective [beta]-stimulants (e.g. isoprenaline), and xanthine broncho dilators (e.g. theophylline, aminophylline and choline theophyllinate); and anticholinergic agents (e.g. ipratropium bromide, oxitropium bromide and tiotropium).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

For example, the dose counter described hereinabove is configured to actuate the dose counter on the forward (downwards) stroke of a medicament canister. Dose counters according to the invention may alternatively be configured to actuate the dose counter of the reverse (upwards) stroke.

The embodiment shown in FIG. 5 is provided with a (separate) second gear wheel with which the second ratchet drive pawl is arranged for engagement. In a variation, the second gear wheel is omitted and the second ratchet drive pawl is arranged for engagement with the ratchet-toothed wheel.

The invention claimed is:

1. A dose counter for counting doses of medicament dispensed by or remaining in a metered-dose inhaler, the dose counter comprising:
   a rotatably mounted first gear wheel having a circular arrangement of ratchet teeth;
   a display coupled to the first gear wheel, the display having a visible array of dose counting indicia indexable in response to rotary motion of the first gear wheel; and
   an actuator mechanism having a first ratchet drive pawl for engaging the ratchet teeth of the first gear wheel in response to the dispensation of a medicament dose,
   wherein the actuator mechanism further comprises a second ratchet drive pawl for engaging the ratchet teeth of a second gear wheel that is coupled to the display, and wherein the actuator mechanism is configured such that, in use of the dose counter for counting a dispensed dose, a first ratchet tooth of the first gear wheel is engaged and rotatably driven by the first ratchet drive pawl and then a second ratchet tooth of the second gear wheel, which is coupled to the display, is engaged and rotatably driven by the second ratchet drive pawl,
   wherein the display comprises a flexible tape arranged between an indexing spool and a stock bobbin,
   wherein the first gear wheel and the second gear wheel are connected together by an axle, which serves as an indexing spool for the display, and
   wherein the first gear wheel and the second gear wheel are arranged at opposite ends of the axle so that either wheel can be used to drive the display.

2. A dose counter according to claim 1, wherein the actuator mechanism further comprises an actuator shaft mounted for linear reciprocating movement in response to the dispensing of a dose of medicament.

3. A dose counter according to claim 1, wherein the actuator mechanism further comprises an actuator shaft mounted for linear reciprocating movement in response to the dispensing of a dose of medicament, the actuator shaft carrying the first ratchet drive pawl.

4. A dose counter as claimed in claim 1, wherein the second ratchet drive pawl is arranged to prevent reverse rotation of the second gear wheel with which it is arranged for engagement.

5. A metered-dose inhaler comprising:
   a medicament canister;
   an actuator body for receiving the canister and having a medicament delivery outlet; and
   the dose counter as claimed in claim 1.

6. The dose counter according to claim 1, wherein a shape of the first ratchet tooth differs from a shape of the second ratchet tooth.

7. A dose counter according to claim 2, wherein the actuator shaft is resiliently biased towards a starting position, the actuator shaft being displaceable against the resilient bias for actuating the dose counter.

8. A dose counter according to claim 3, wherein the second gear wheel includes a circular arrangement of gear teeth.

9. A dose counter according to claim 3, wherein the actuator mechanism is configured such that, in use of the dose counter for counting a dispensed dose:
   a first ratchet tooth of the first gear wheel is engaged and rotatably driven by the first ratchet drive pawl until the second ratchet drive pawl has traveled over the tip of a second ratchet tooth of the second gear wheel with which the second ratchet drive pawl is arranged for engagement; and then the second ratchet tooth is engaged and rotatably driven by the second ratchet drive pawl.

10. A dose counter according to claim 8, wherein the second ratchet drive pawl is resiliently biased into contact with the gear teeth of the second gear wheel with which it is arranged for engagement, the second ratchet drive pawl being displaceable away from the second gear wheel against the bias.

11. The dose counter according to claim 10, wherein the first ratchet drive pawl is displaceable away from the first gear wheel against a bias, and the first ratchet drive pawl is biased in an opposite direction to the bias of the second ratchet drive pawl.

12. A method of counting doses dispensed from or remaining in a metered-dose inhaler, the dose counter including:
   a rotatably mounted first gear wheel having a circular arrangement of ratchet teeth;
   a display coupled to the first gear wheel, the display having a visible array of dose counting indicia indexable in response to rotary motion of the first gear wheel; and
   an actuator mechanism having a first ratchet drive pawl for engaging the ratchet teeth of the first gear wheel in response to the dispensation of a medicament dose, and a second ratchet drive pawl for engaging the ratchet teeth of a second gear wheel that is coupled to the display, wherein the first gear wheel and the second gear wheel are connected together by an axle, which serves as an indexing spool for the display, said method comprising;
engaging and rotatably driving a first ratchet tooth of the first gear wheel with the first ratchet drive pawl; and
engaging and rotatably driving a second ratchet tooth of the second gear wheel that is coupled to the display with the second ratchet drive pawl.

\* \* \* \* \*